United States Patent

Wong et al.

[11] Patent Number: 5,197,873
[45] Date of Patent: * Mar. 30, 1993

[54] ORTHODONTIC BRACKET AND METHOD

[75] Inventors: Rayond F. Wong, Chino; Patrick D. Kidd, San Dimas; Farrokh Farzin-Nia, Inglewood, all of Calif.

[73] Assignee: Ormco Corporation, Glendora, Calif.

[*] Notice: The portion of the term of this patent subsequent to Dec. 10, 2008 has been disclaimed.

[21] Appl. No.: 804,806

[22] Filed: Dec. 9, 1991

Related U.S. Application Data

[63] Continuation of Ser. No. 677,377, Mar. 27, 1991, Pat. No. 5,071,344, which is a continuation-in-part of Ser. No. 241,193, Sep. 7, 1988, abandoned.

[51] Int. Cl.$^5$ ............................................... A61C 3/00
[52] U.S. Cl. ..................................................... 433/9
[58] Field of Search ............................ 433/8, 9; 228.1

[56] References Cited

U.S. PATENT DOCUMENTS

| | | | |
|---|---|---|---|
| 4,165,561 | 8/1979 | Miller et al. | 433/9 |
| 4,204,325 | 5/1980 | Kaelble | 433/9 |
| 4,340,529 | 7/1982 | Lee, Jr. et al. | 433/9 |
| 4,479,782 | 10/1984 | Orlowski et al. | 433/9 |
| 4,752,221 | 6/1988 | Hanson et al. | 433/9 |
| 4,784,606 | 11/1988 | Jones et al. | 433/8 |
| 4,801,528 | 1/1989 | Bennett | 433/9 |
| 4,838,786 | 6/1989 | Reher et al. | 433/9 |

Primary Examiner—John J. Wilson
Attorney, Agent, or Firm—Wood, Herron & Evans

[57] ABSTRACT

An orthodontic bracket having a base portion for attachment to a tooth. The base portion is provided with a substantially monolayer of substantially uniform sized particles. The particles may have a size in the range of 5 to 200 micron.

41 Claims, 2 Drawing Sheets

ORTHODONTIC BRACKET AND METHOD

This is a continuation of application Ser. No. 07/677,377, filed Mar. 27, 1991, now U.S. Pat. No. 5,071,344, which is a continuation-in-part of application Ser. No. 07/241,193, filed Sep. 7, 1988, now abandoned.

BACKGROUND OF THE INVENTION

The present invention relates to orthodontic brackets.

Orthodontic brackets have been generally made of metal and are typically bonded directly to the teeth of a patient. It has always been important to provide a good bonding between the orthodontic bracket and the tooth. Over the years many improvements have been made to metal brackets and the adhesive used to bond the metal bracket to the teeth. As a result, the bonding of typical prior art metal brackets to the teeth has reached generally acceptable values. Aesthetic brackets have recently become popular. Typically these brackets made of a ceramic material which is much more difficult to secure directly to the teeth. In order to overcome the difficulty in obtaining a good bond with a bracket made of a single crystal alumina, a method of applying such brackets has been suggested in U.S. Pat. No. 4,681,538. However, such a method requires special handling and care to obtain acceptable bonding strength. The provision of undercuts within the base of the bracket has also been suggested. While the provision of such undercuts in the base has provided improved bonding strength, it does not provide the same strength as typical prior art metal brackets. In addition, certain adhesives have been found to detract from the transparent or translucent characteristic of the new aesthetic brackets.

Applicants have invented an improved orthodontic bracket and method of making such wherein improved bonding strength may be obtained without detracting from the aesthetic qualities of the bracket.

SUMMARY OF THE INVENTION

In one aspect of the present invention, there is provided an orthodontic bracket having a base portion for attachment to a tooth. The base portion is provided with a substantially monolayer of substantially uniform sized particles. The particles may have a size in the range of 5 to 200 microns.

In another aspect of the present invention, there is provided a method of applying a substantially monolayer of particles of substantially uniform size to the contact surface of an orthodontic bracket comprising the steps of:

applying a layer of a adhesive to the contact surface of an orthodontic bracket, said adhesive having an organic binder, activator and surfactant;

applying a monolayer of particles of substantially uniform size to said tooth contact surface; and subjecting said brackets to heat so as to diffusion bond the particles to said tooth contact surface.

In yet another aspect of the present invention, there is provided a adhesive for applying to the contact surface of an orthodontic bracket for use in heat bonding particles thereto. The adhesive comprises a mixture of an organic binder which is substantially tacky at room temperature, a activator and surfactant.

DETAILED DESCRIPTION

Figure 1:
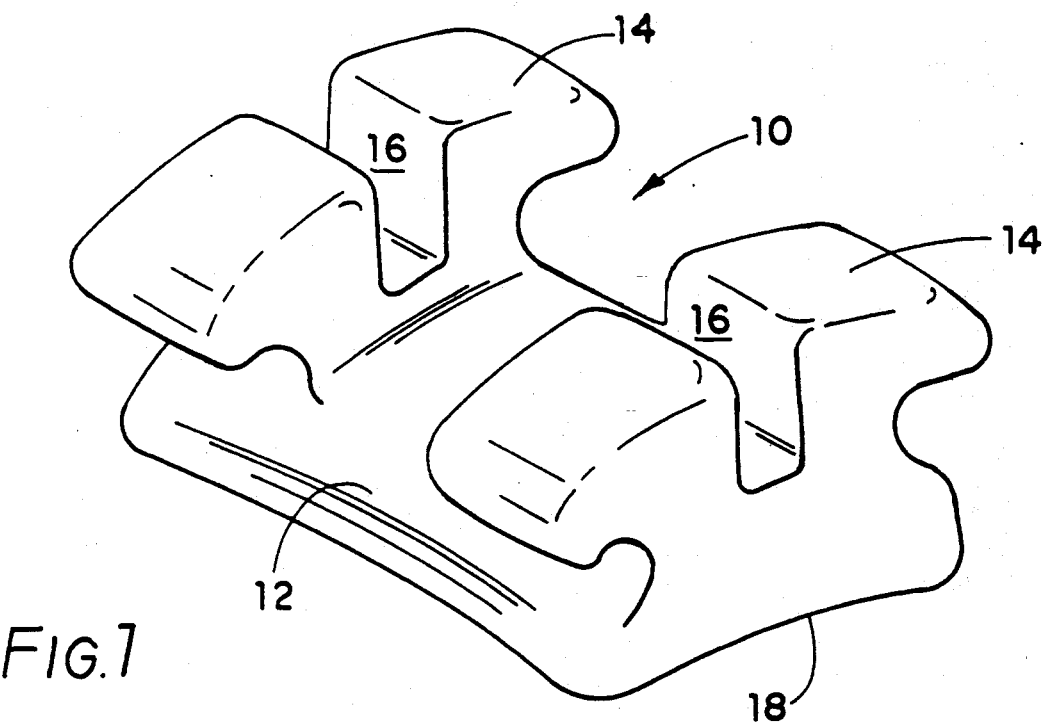
FIG. 1 is a top perspective view of an orthodontic bracket made in accordance with the invention illustrated in the bonding base.
Figure 2:
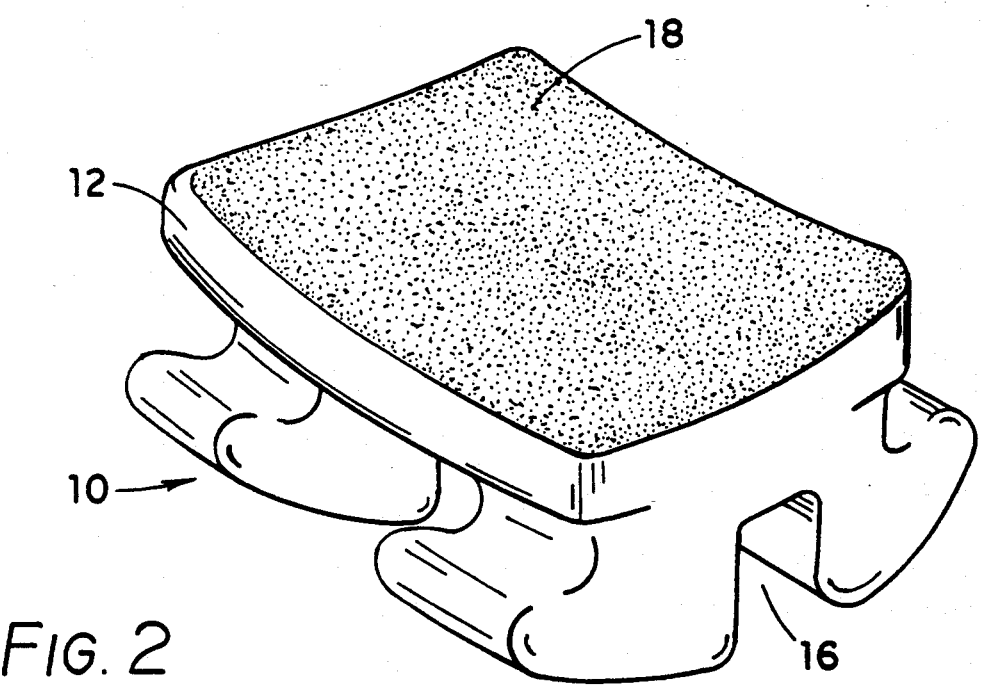
FIG. 2 is a bottom perspective view of the orthodontic bracket of FIG. 1.
Figure 3:
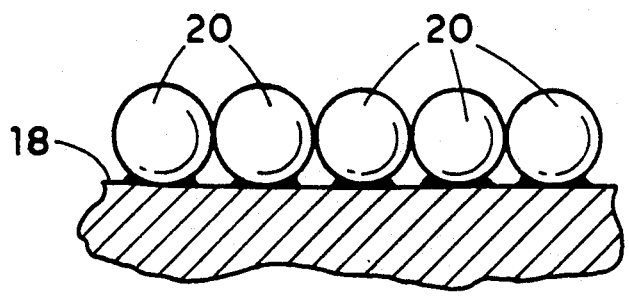
FIG. 3 is a greatly enlarged partial front elevational view of the bonding base of the bracket of FIG. 1.
Figure 4:
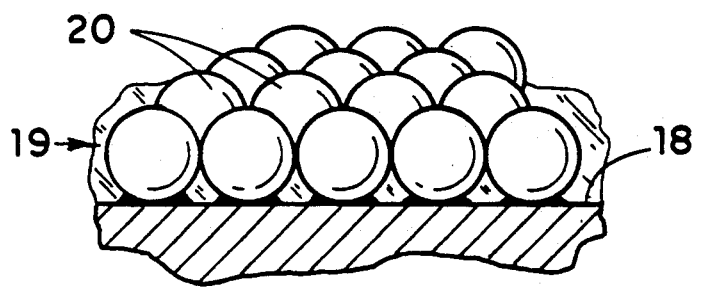
FIG. 4 is a greatly enlarged perspective view of the bonding vase of the bracket of FIG. 1.

Referring to FIGS. 1 to 4, there is illustrated orthodontic bracket 10 for attachment directly to a tooth of a patient made in accordance with the present invention. The orthodontic bracket comprises a base portion 12 and a pair of tiewings 14 which extend from the base portion 12. Tiewings 14 are each provided with an elongated slot 16 for receiving an orthodontic archwire (not shown). Preferably the orthodontic bracket is made of ceramic material that is transparent or translucent. In the particular embodiment illustrated the orthodontic bracket 10 is made of a single crystal alumina material. The base 12 has a tooth contact surface 18 for placement against the surface of a tooth of a patient. Surface 18 is provided with a substantially monolayer 19 of individual particles 20 (as can best be seen in FIGS. 3 and 4) of substantially uniform size secured thereto having a size in the range of 5 microns to 200 microns. Preferably the particles 20 are substantially spherical in shape as illustrated. In the preferred embodiment illustrated, the particles 20 comprise substantially spherical hollow balls made of zirconium oxide. An example of such may be purchased from Metco under the tradename AE-7078. The particles 20 forming monolayer 19 are of substantially uniform size such that the small particles do not completely fill the voids that exist between adjacent particles 20. Preferably, the size variation of particles 20 in layer 19 is such that the smaller particles 20 are not less than about 75% of the size of the larger particles 20, most preferably, not less than about 85%. If the size variation is too great, it will cause the particles to be too closely packed and thus, detract from the aesthetic qualities of the bracket. In the particular embodiment illustrated, the size of particles 20 for layer 19 is in the range of about 37 to 44 microns.

Figure 5:
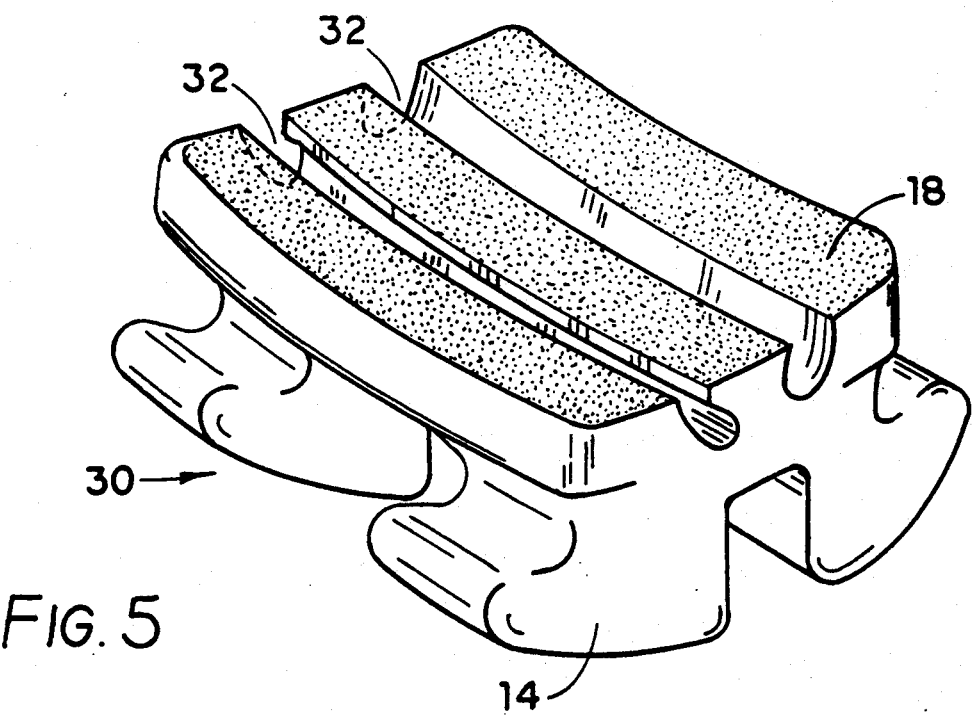
FIG. 5 is a bottom perspective view of another embodiment of a bracket made in accordance with the present invention.

In the particular embodiment illustrated in FIGS. 1–4, the surface 18 of base 12 is substantially continuous. However, the present invention is not so limited. Referring to FIG. 5, there is illustrated a modified bracket 30 made in accordance with the present invention. The bracket 30 is substantially identical to bracket 10 of FIG. 1–4, like numerals represent like part, except that grooves 32 are provided in the surface 18 which may be present in certain brackets for improving adhesion.

While irregular shaped particles may be used to obtain better bonding, they do not provide as aesthetically pleasing appearance when used on aesthetic brackets, for example, brackets made from crystalline alumina.

As previously stated, particles 20 are secured to the contact surface 18 so that they will be permanently attached thereto. In the particular embodiment illustrated the particles 20 are diffusion bonded (welded) to the contact surface 18. The following table illustrates the improved bond strengths obtained with an orthodontic bracket made of single crystalline alumina having particles 20 applied to surface 18 in accordance with the present invention in comparison with a single crystalline alumina bracket without particles 20 and to a standard orthodontic metal bracket. The prior art and present invention single crystalline aluminum brackets were tested with and without grooves provided in surface 18. The crystalline alumina brackets with grooves being similar to that illustrated in FIG. 5 and the crystalline alumina brackets without grooves being similar to that illustrated in FIG. 1-4. The metal bracket and many prior art single crystal alumina grooved brackets were bonded to the tooth using typical prior art adhesives. In the present instance, a two part dimethacrylate adhesive as sold by Ormco under the tradename Challenge. A light cure adhesive sold by Scientific Pharmaceuticals was used to bond the crystalline aluminum brackets to the teeth.

tially uniform mixture wherein the binder and activator are in suspension. Also, it is important that not too much activator be used as this can cause wicking during heating which will result in deformation of the particle and filling the voids therebetween. The organic binder in the particular embodiment illustrated was purchased from Cotronics, of Brooklyn, N.Y.; the activator used is sold under the tradename CERAMCOAT 512-T by Aremco of Ossining, N.Y. and the surfactant used was purchased from ICI under the tradename SPAN 85. The adhesive mixture is applied to the contact surface 18 either by brushing or spraying. Preferably the film thickness is obtained between 0.001 to 0.005 inches. The adhesive mixture is allowed to dry at room temperature for approximately 1 to 5 minutes. The adhesive after drying is still tacky. Thereafter particles 20 are either sprinkled on the contact surface 18 or the bracket 10 is turned over and the contact surface 18 is tamped into a pile of particles 20 such that a dense monolayer 19 of

|  | Standard Metal Bracket | Prior Art Single Crystal Alumina Bracket | | Present Invention Single Crystal Alumina Bracket | |
| --- | --- | --- | --- | --- | --- |
|  |  | with groove | without groove | with groove | without groove |
| Bond Strength | 150 kg/cm$^2$ | 75 kg/cm$^2$ | 67 kg/cm$^2$ | 180 kg/cm$^2$ | 207 kg/cm$^2$ |

As can be seen from the foregoing table, the standard metal bracket had a bond strength of 150 kg/cm$^2$ and the orthodontic bracket having grooves in the base made of single crystal alumina of the prior art had a bond strength of 75 kg/cm$^2$ and an orthodontic bracket have grooves in the base made of single crystal alumina with grooves made in accordance with the present invention had a bond strength of 180 kg/cm$^2$. It can be seen that the single crystal alumina bracket without grooves in the base, but having monolayer of particles in accordance with the present invention also provided improved results over the typical prior art metal bracket. Thus avoiding the necessity of providing grooves to improve bond strength. The bond strengths of brackets made in accordance with the present invention as compared to a prior art single crystal alumina bracket and typical metal brackets was substantially improved.

It is important that the particles 20 are securely adhered to the surface 18 of the bracket 10. Applicants have found the following procedure to be quite effective in obtaining a substantially monolayer 19 of particles 20 made of zirconium oxide having a size range from about 37 to 44 microns diffusion bonded to the contact surface 18 of bracket 10 made of single crystal alumina. First, the bracket 10 is inverted such that the contact surface 18 faces upward. Then, an adhesive is applied to the contact surface 18. This adhesive has the general consistency such that it can be brushed or sprayed on. The adhesive comprises a mixture of an organic binder, a activator and surfactant. For the purpose of the present invention, an activator is a material used to activate (lower the activation energy) required for diffusion bonding below the melting point of the particles 20 and bracket 10. The organic binder and activator are mixed together along with a sufficient amount of surfactant so as to permit mixing thereof. In the particular formulation, the organic binder comprised about 72.3% by weight of the mixture, the activator comprised about 24.1% by weight and the surfactant comprised about 3.6% by weight. It is important that a proper mix is obtained so as to provide a substantially particles is provided. The tacky organic binder allows the spheres to be placed and held in position on the contact surface 18. Thereafter, the bracket is placed in a furnace and preheated to about 120° C. in air and then the furnace is heated to approximately 600° C. Typically, the organic binder will burn off at approximately 600° C. Preferably, the temperatures within the furnace is increased an at a substantially constant ramp function so as not to disturb the location of the particles 20. Preferably, no greater than a rate of 15° C./min. The typical time frame to heat the particles to 600° C. from ambient is approximately 30 to 60 minutes. Thereafter, the orthodontic bracket is heated to a second higher temperature below the melting temperature of the bracket. In the particular embodiment illustrated the orthodontic bracket 10, which is made of a single crystal alumina, has a melting temperature in the range of 2050° to 2100° C. The temperature of the furnace is increased to approximately 1600° C. It is important that the furnace temperature not be too high as this can cause deformation of the particles, filling the voids therebetween and the temperature not be too low as this can result in insufficient bonding of the particles 22 to the surface 18. A suitable range can be easily obtained by simply taking several samples until acceptable values are obtained. The activator used in the adhesive mixture causes the particles 20 to be diffusion bonded "welded" to the surface 18 at the contact points at a temperature substantially below its melting point. The orthodontic bracket is maintained at this temperature for a sufficient time period to allow diffusion bonding. Typically for about 30 to 60 minutes. Thereafter the bracket is cooled and removed from the furnace.

Applicants have found that this procedure provides a very high degree of bonding between the particles 20 and the surface 18 of orthodontic bracket 10 without any substantial distortion to the particles 10. Preferably, the particles 20 are made of a material having a coefficient of expansion substantially the same as the orthodontic bracket.

An appropriate orthodontic adhesive is then applied to surface 18 and the bracket 10 secured to the tooth as is customarily done in the prior art. A suitable adhesive that can be used is sold by Ormco under the tradename Challenge. However, many other suitable adhesives may be used. Because of the improved bonding strengths obtained through the use of the present invention, a wider variety of adhesive will be available for the orthodontist.

It is to be understood that different combinations of materials may be used for the bracket 10 and/or particles 20 and that certain modifications with respect to manufacturing brackets may be desired or necessary. In the manufacture of an orthodontic bracket made of a polycrystalline alumina material (i.e. such as may be purchased from General Electric Company) having hollow zirconium oxide particles bonded to the contact surface 18. Suitable zirconium oxide particles may be purchasee from Metco under the tradename AE-7078, having a size range from about 37-44 micron as previouly discussed. Certain modifications to the manufacture of the bracket may be desirable for aesthetic reasons. The particles 20 would be placed on the contact surface 18 of the bracket 10 in the same manner previously discussed with regard to the single crystalline alumina bracket. After the particles have been placed on the base, it would be placed in a furnace having an oxygen containing environment, for example air, and heated to a temperature of approximately 650° C. for approximately 1 hour to burn off any organic binders. As with the single crystalline alumina bracket, this temperature may vary in accordance with the temperature required to burn off the specific organic binder. After this has been done, the bracket is allowed to cool and then placed in a second furnace having a hydrogen environment and then heated to a temperature of approximately 1800° C. The bracket is maintained at this temperature for approximately 1 hour in order to diffusion bond the particles 20 thereto. Since polycrystalline alumina becomes opaque in an air environment at temperatures necessary for diffusion bonding to occur, it is necessary to place the bracket in a furnace having a hydrogen environment. Preferably, the furnace is lined with tungsten or a high purity alumina to minimize any potential discoloration of the polycrystalline alumina bracket. An appropriate furnace may be purchased from CM Furnaces, Inc. of Bloomfield, N.J. After the particles 20 have been properly diffusion bonded to the contact surface 18, the bracket is allowed to cool after which it is removed from the furnace. Applicants have found that certain impurities in the zirconium oxide particles results in a slight discoloration of the particles during the diffusion bonding process. In order to restore the clarity to the balls, the orthodontic bracket 10 is subjected to a third heat treatment process wherein the orthodontic bracket is placed in a furnace having an oxygen-containing environment, for example, air, and is heated to a temperature of approximately 650° C. to oxidize any impurities that may be present and thus restoring the particles 10 to a high degree of clarity. Thereafter, the brackets are removed from the furnace and allowed to cool. The brackets are then secured to the tooth of the patient by using normal bonding techniques presently available, i.e., by the placement of an appropriate adhesive between the tooth contact surface of the bracket and tooth.

It is to be understood that the various other changes and modifications can be made without the particle in the spirit and scope of the present invention. That particular scope of the present invention be limited by the attached claims.

We claim:

1. An orthodontic bracket having a base portion for attachment to a tooth, said base portion being made of a ceramic material and having a tooth contact surface, said base portion having particles made of a ceramic material diffusion bonded to said tooth contact surface with an activator which reduces the temperature at which said particles are diffusion bonded to said tooth contact surface, said particles having a size in the approximate range of 20-200 microns to provide mechanical undercuts to produce void spaces between the particles which can be penetrated by flowable cement to establish mechanical retention interlocks when the particle-covered tooth contact surface of the base portion is cemented to a tooth and said particles having sufficient size uniformity to avoid substantial filling of said void spaces with small particles.

2. An orthodontic bracket according to claim 1 wherein said particles are substantially hollow and spherical in shape.

3. An orthodontic bracket according to claim 1 wherein said base portion is made of a substantially transparent ceramic material.

4. An orthodontic bracket according to claim 1 wherein the coefficient of expansion of said particles and said base portion are sufficiently similar so as to avoid separation of said particles from said base portion when a temperature variation of about 1200° C. is experienced.

5. An orthodontic bracket according to claim 1 wherein said orthodontic bracket is made of crystalline alumina.

6. An orthodontic bracket according to claim 5 wherein said particles are made of a crystalline alumina.

7. An orthodontic bracket according to claim 1 wherein said particles have a size in the range of 30-50 microns.

8. An orthodontic bracket having a base portion for attachment to a tooth, said base portion having a tooth contact surface, said base portion having particles diffusion bonded to said tooth contact surface with an activator which reduces the temperature at which said particles are diffusion bonded to said tooth contact surface, said particles having a size in the approximate range of 20-200 microns to provide mechanical undercuts to produce void spaces between the particles which can be penetrated by flowable cement to establish mechanical retention interlocks when the particle-covered tooth contact surface of the base portion is cemented to a tooth and said particles having sufficient size uniformity to avoid substantial filling of said void spaces with small particles.

9. An orthodontic bracket according to claim 8 wherein said particles are substantially hollow and spherical in shape.

10. An orthodontic bracket according to claim 8 wherein the coefficient of expansion of said particles and said base portion are sufficiently similar so as to avoid separation of said particles from said base portion when a temperature variation of about 1200° C. is experienced.

11. An orthodontic bracket according to claim 8 wherein said particles have a size in the range of 30-5-0-200 microns.

12. A method of improving the bonding characteristics of an orthodontic bracket comprising the steps of:

a) applying a layer of an adhesive to the contact surface of an orthodontic bracket, said adhesive including an activator;
b) applying particles to said tooth contact surface; and
c) subjecting said bracket to a temperature substantially below the melting point of said particles whereby said activator causes said particles to be diffusion bonded to said tooth contact surface with the activator, said particles having a size in the approximate range of 20–200 microns to provide mechanical undercuts to produce void spaces between the particles which can be penetrated by flowable cement to establish mechanical retention interlocks when the particle-covered tooth contact surface of the bracket is cemented to a tooth and said particles having sufficient size uniformity to avoid substantial filling of said void spaces with small particles.

13. An orthodontic bracket comprising a ceramic base portion for attachment to a tooth, said base portion having a tooth contact surface to which at least one exposed outer layer of ceramic particles are bonded by elevation of the temperature of the particles and base portion to a point substantially below the melting point of the particles and base portion with an activator located therebetween, said bonded particles being substantially free of thermally-induced distortion and providing mechanical undercuts to establish void spaces between the particles which can be penetrated by flowable cement to establish mechanical retention interlocks when the particle-covered tooth contact surface of the base is cemented to a tooth, said bonded particles having a size in the approximate range of 20–200 microns and having sufficient size uniformity to avoid substantial filling of said void spaces with small particles.

14. An orthodontic bracket according to claim 13 wherein said particles are substantially spherical in shape.

15. An orthodontic bracket according to claim 14 wherein said particles are substantially hollow.

16. An orthodontic bracket according to claim 13 wherein the coefficient of expansion of said ceramic particles and said base portion are sufficiently similar to avoid debonding of said particles from said base portion when a temperature variation of approximately 1200° C. is experienced.

17. An orthodontic bracket according to claim 13 wherein said base portion is made of a substantially transparent ceramic material.

18. An orthodontic bracket according to claim 13 wherein said orthodontic bracket is made of crystalline alumina.

19. An orthodontic bracket according to claim 13 wherein said particles are made of crystalline alumina.

20. An orthodontic bracket according to claim 13 wherein said base portion and particles are crystalline alumina.

21. An orthodontic bracket according to claim 13 wherein said particles are zirconium oxide.

22. An orthodontic bracket according to claim 13 wherein said base portion is polycrystalline alumina.

23. An orthodontic bracket according to claim 22 wherein said particles are zirconium oxide.

24. An orthodontic bracket according to claim 13 wherein said particles have a size in the approximate range of 30–50 microns.

25. An orthodontic bracket according to claim 13 wherein said particles are substantially irregularly shaped.

26. A method of improving the bonding characteristics of an orthodontic bracket having a ceramic base portion provided with a tooth contact surface, comprising the steps of:
a) applying ceramic particles to the contact surface of the ceramic base portion of the orthodontic bracket, with an activator disposed therebetween,
b) elevating the temperature of the ceramic bracket base portion and particles to a bonding temperature substantially below the melting point of said particles and base portion to bond the particles and tooth contact surface with the activator without substantial thermally-induced distortion of the particles, the bonded particles providing mechanical undercuts to establish void spaces between the particles which can be penetrated by flowable cement to establish mechanical retention interlocks when the bonded particle-covered tooth contact surface of the base is cemented to a tooth, the particles having a size in the approximate range of 20–200 microns and having sufficient size uniformity to avoid substantial filling with small particles of void spaces between adjacent particles established by the undercuts.

27. The method of claim 26 wherein said particle-applying step includes applying substantially spherical particles to the base portion.

28. The method of claim 26 wherein said particle-applying step includes applying substantially hollow spherical particles to the base portion.

29. The method of claim 26 wherein the particle-applying step includes applying particles having a coefficient of expansion sufficiently similar to the coefficient of expansion of the base portion to avoid debonding of the particles and base portion when the bonded particles and base portion are subjected to a temperature change of 1200° C.

30. The method of claim 26 wherein the particles are applied to a base portion made of transparent ceramic material.

31. The method of claim 26 wherein the particle-applying step includes applying particles to a crystalline alumina base portion.

32. The method of claim 26 wherein the particle-applying step includes applying crystalline alumina particles to the base portion.

33. The method of claim 26 wherein said particle-applying step includes applying crystalline alumina particles to a crystalline alumina base portion.

34. The method of claim 26 wherein the particle-applying step includes applying zirconium oxide particles to the base portion.

35. The method of claim 26 wherein the particle-applying step includes applying particles to a polycrystalline base.

36. The method of claim 26 wherein the particle-applying step includes applying zirconium oxide particles to a polycrystalline base portion.

37. The method of claim 26 wherein said particle-applying step includes applying particles sized in the approximate range of 30–50 microns.

38. The method of claim 26 wherein said temperature elevating step includes elevating the temperature of the ceramic particles and base portion to a bonding temperature in the approximate range of 1000° C.–1850° C.

39. The method of claim 26 wherein the ceramic particles are zirconium oxide and the ceramic base portion is polycrystalline alumina and the temperature elevating step includes subjecting the ceramic particles and base portion to a hydrogen atmosphere while the particles and base portion are at the elevated bonding temperature.

40. The method claim 39 further comprising the step of subjecting the ceramic base portion and bonded particles to a temperature of approximately 650° C. in an oxygen-containing environment to oxidize any impurities that may be present and restore the particles to a high degree of clarity.

41. The method of claim 26 wherein said particle-applying step includes applying substantially irregularly shaped particles to the base portion.

* * * * *

UNITED STATES PATENT AND TRADEMARK OFFICE
CERTIFICATE OF CORRECTION

PATENT NO. : 5,197,873
DATED : March 30, 1993
INVENTOR(S) : Raymond F. Wong et al.

It is certified that error appears in the above-indentified patent and that said Letters Patent is hereby corrected as shown below:

On the title page: Item [63]

-- Continuation of Ser. No. 677,377, Mar. 27, 1991, Pat. No. 5,071,344, which is a file wrapper continuation of Ser. No. 476,355, Feb. 7, 1990, abandoned, which is a continuation-in-part of Ser. No. 241,193, Sep. 7, 1988, abandoned--

At column 6, lines 65-66, "30-5-0-200" should be --30-50 microns--.

Signed and Sealed this

Twenty-sixth Day of July, 1994

*Attest:*

BRUCE LEHMAN

*Attesting Officer*     *Commissioner of Patents and Trademarks*